(12) United States Patent
Casano

(10) Patent No.: US 11,576,839 B2
(45) Date of Patent: Feb. 14, 2023

(54) THERAPEUTIC POUCH FOR CONCEALING INTRAVENOUS THERAPY EQUIPMENT

(71) Applicant: Ella Kathleen Casano, Fairfield, CT (US)

(72) Inventor: Ella Kathleen Casano, Fairfield, CT (US)

( * ) Notice: Subject to any disclaimer, the term of this patent is extended or adjusted under 35 U.S.C. 154(b) by 831 days.

(21) Appl. No.: 16/543,073

(22) Filed: Aug. 16, 2019

(65) Prior Publication Data

US 2020/0146933 A1 May 14, 2020

Related U.S. Application Data

(60) Provisional application No. 62/687,065, filed on Jun. 19, 2018.

(51) Int. Cl.
| | |
|---|---|
| *A61J 1/16* | (2006.01) |
| *A61J 1/14* | (2006.01) |
| *A61M 5/14* | (2006.01) |
| *A61J 1/10* | (2006.01) |
| *A63H 3/00* | (2006.01) |
| *A63H 3/02* | (2006.01) |

(52) U.S. Cl.
CPC .............. *A61J 1/16* (2013.01); *A61J 1/1462* (2013.01); *A63H 3/005* (2013.01); *A63H 3/02* (2013.01); *A61J 1/10* (2013.01); *A61M 5/1415* (2013.01); *A61M 5/1417* (2013.01)

(58) Field of Classification Search
CPC ............ A61M 2205/59; A61M 5/1415; A61M 5/1417; A61M 5/1414; A63H 3/005; A63H 3/02; A63H 3/003; A63H 3/50; A61J 1/1462; A61J 1/16; A61J 1/10; A61J 1/00; A61J 9/0607; A61J 9/0638; A61J 9/0661
See application file for complete search history.

(56) References Cited

U.S. PATENT DOCUMENTS

| | | | | |
|---|---|---|---|---|
| 4,735,613 A | * | 4/1988 | Bellin ................. | A61M 5/1483 D24/111 |
| 5,776,105 A | * | 7/1998 | Corn ................... | A61M 5/1483 604/179 |
| 7,021,825 B1 | * | 4/2006 | Schultz ................. | A47D 15/00 224/438 |
| 8,152,587 B1 | * | 4/2012 | Brown ................... | A63H 3/005 446/76 |

(Continued)

*Primary Examiner* — Adam Marcetich
(74) *Attorney, Agent, or Firm* — Dunlap Bennett & Ludwig, PLLC

(57) ABSTRACT

A therapeutic pouch is provided. The therapeutic pouch defines a cavity for slidably receiving intravenous therapy equipment, such as an IV bag or other fluid dispenser. A front portion of the therapeutic pouch provides a comforting presentation for the patient, while the rear portion of the therapeutic pouch provides a visibility pouch for securing the IV bag and allowing a healthcare provider visibility of the administration of the fluids retained by the IV bag. The visibility pouch may provide an upper opening and an opposing lower opening, both communicating with the cavity for enabling the IV bag to protrude therefrom and access to IV tubing and ports, respectively. An upper portion of the therapeutic pouch provides a hanging loop for working in unison with the IV bag hole for enabling support from an IV stand or the like.

7 Claims, 4 Drawing Sheets

(56) References Cited

U.S. PATENT DOCUMENTS

| | | | | |
|---|---|---|---|---|
| 2008/0032594 A1* | 2/2008 | Magener | ............... | A63H 3/005 |
| | | | | 446/369 |
| 2008/0054132 A1* | 3/2008 | Muncie | ............... | A61M 5/1415 |
| | | | | 248/176.1 |
| 2008/0096459 A1* | 4/2008 | Mingle | ................. | A63H 3/005 |
| | | | | 446/74 |
| 2008/0139076 A1* | 6/2008 | Frasier-Scott | ......... | A61M 5/14 |
| | | | | 446/72 |
| 2013/0137338 A1* | 5/2013 | Rubinfeld | ................ | A47K 7/02 |
| | | | | 446/73 |
| 2013/0324006 A1* | 12/2013 | Marshall | ............... | A61J 9/0607 |
| | | | | 446/369 |
| 2017/0246546 A1* | 8/2017 | Brown, Sr. | ............. | A63H 3/02 |
| 2017/0296939 A1* | 10/2017 | Rivera | ..................... | A61J 1/16 |
| 2018/0290063 A1* | 10/2018 | Wang | ..................... | A63H 3/003 |
| 2019/0192980 A1* | 6/2019 | Vogel | .................... | A63H 3/005 |
| 2019/0336872 A1* | 11/2019 | Brown, Sr. | ......... | B65D 81/365 |

\* cited by examiner

THERAPEUTIC POUCH FOR CONCEALING INTRAVENOUS THERAPY EQUIPMENT

CROSS-REFERENCE TO RELATED APPLICATION

This application claims the benefit of priority of U.S. provisional application No. 62/687,065, filed 19 Jun. 2018, the contents of which are herein incorporated by reference.

BACKGROUND OF THE INVENTION

The present invention relates to intravenous therapy accessories and, more particularly, to a therapeutic pouch for concealing an intravenous therapy dispenser (such as an IV bag or other delivery apparatus of medicinal or blood product for delivery directly into the veins of a user of intravenous therapy). The therapeutic pouch can embody a stuffed animal that conceals the dispenser to the recipient of the intravenous therapy, while allowing manual and visual access to the dispenser by healthcare providers.

Many children need to receive intravenous (IV) infusions or injections but are afraid of all the medical equipment involved, especially when that equipment, such as IV bags, are constantly looming over them for extended periods of time. Current solutions to this problem do not conceal any medical devices, do not provide a comforting visual presentation, and/or are makeshift and thus not reusable.

As can be seen, there is a need for a therapeutic pouch for concealing an IV bag or the like, wherein the therapeutic pouch can embody a stuffed animal that conceals the dispenser to the recipient of the intravenous therapy, while allowing manual and visual access to the dispenser by healthcare providers. The therapeutic pouch embodied is designed to be very visually appealing to a child, by presenting a front-facing stuffed animal, thereby fostering a feeling of comfort and familiarity for the child with its use. The therapeutic pouch is adapted to be reused for a plurality of intravenous administrations.

Specifically, the present invention hides the IV bag of medicine or blood product from the patient's sight from the front, concealing the IV bag inside a friendly looking pouch/sleeve, helping the patient feel more relaxed in their surroundings, while also allowing the doctor or nurse to see through the visibility sleeve or backing to monitor the proper administration by way of the IV bag.

In sum, the present invention provides the following: first, a pleasant visual experience for the patient; second, a method of hiding the IV bag used for administering the drip, while allowing the doctor of nurse to view the medication through the back; and third, a reusable product allowing the present invention to become a comfort object during a time of unfamiliar, often stressful or scary medical procedures or infusions, especially for a child.

SUMMARY OF THE INVENTION

In one aspect of the present invention, a therapeutic pouch includes the following: a front portion, a rear portion, a lower portion, and an upper portion defining an inner cavity, wherein the inner cavity dimensioned to house an intravenous bag; the front portion providing a stuffed animal shape; a rear portion substantially defined by a void; and a visibility material extending between opposing peripheries of the void.

In another aspect of the present invention, the therapeutic pouch includes the following: a front portion, a rear portion, a lower portion, and an upper portion defining an inner cavity, wherein the inner cavity dimensioned to house an intravenous bag; the front portion providing a stuffed animal shape; a rear portion substantially defined by a void; a mesh material extending between opposing peripheries of the void, wherein the mesh material defines a sleeve having an upper opening and an opposing lower opening, both openings communicating with the inner cavity; and a hanging loop in the upper portion, wherein the hanging loop aligns with the intravenous bag housed in the inner cavity.

In yet another aspect of the present invention, a method of comforting a patient of intravenous therapy includes the following: providing an intravenous bag for the patient of intravenous therapy; sliding the intravenous bag into the cavity so that the hanging loop aligns associates with a hanging hole of the intravenous bag; and sliding the hanging loop and the hanging hole on a hook of a stand associated with the intravenous therapy so that the stuffed animal shape is facing the patient.

These and other features, aspects and advantages of the present invention will become better understood with reference to the following drawings, description and claims.

DETAILED DESCRIPTION OF THE INVENTION

Figure 1:
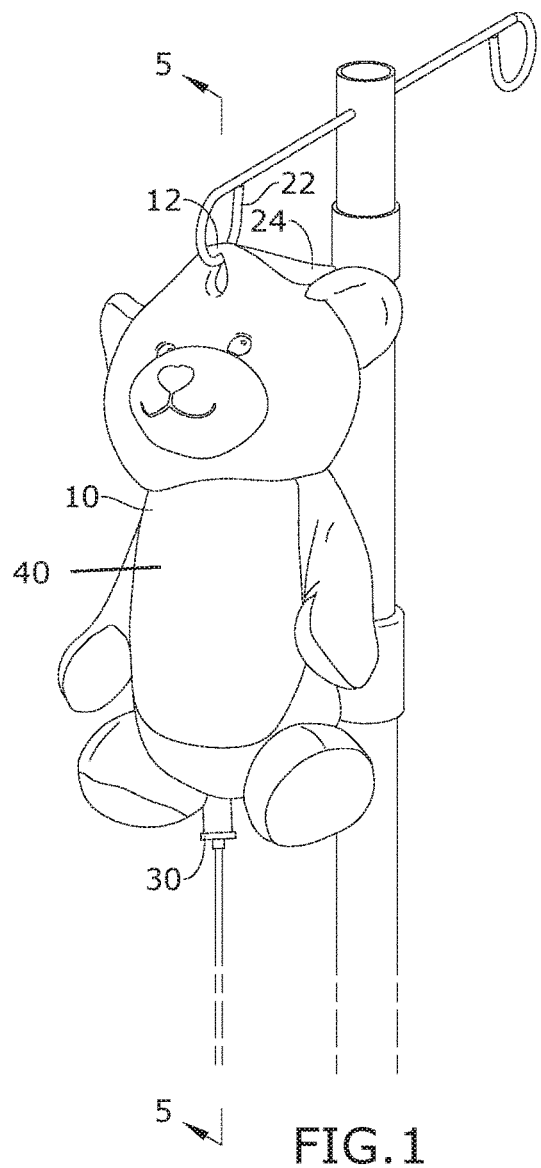
FIG. 1 is a front perspective view of an exemplary embodiment of the present invention shown in use.
Figure 2:
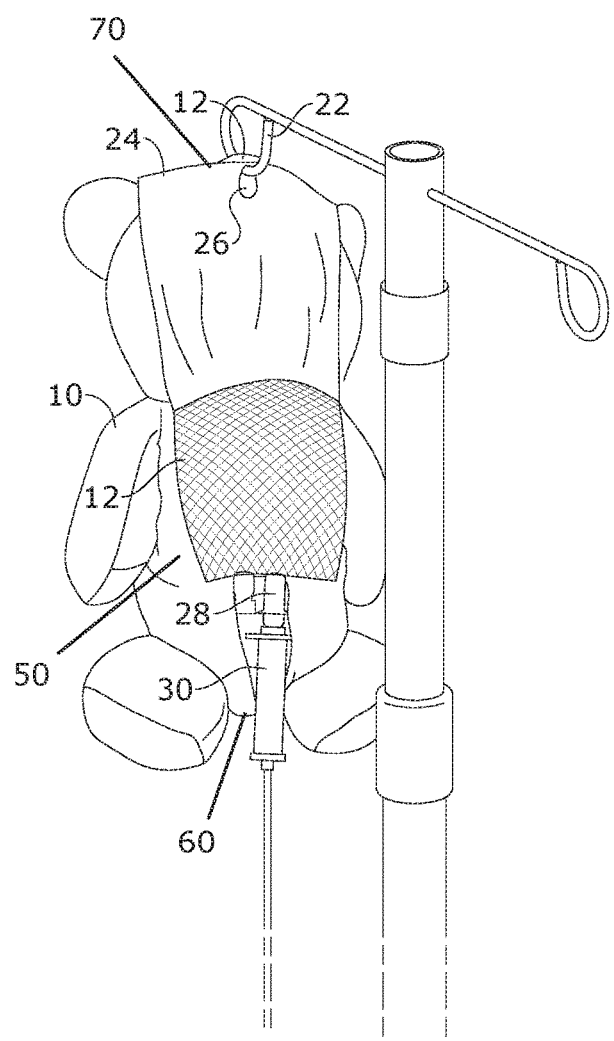
FIG. 2 is a rear perspective view of an exemplary embodiment of the present invention shown in use.
Figure 3:
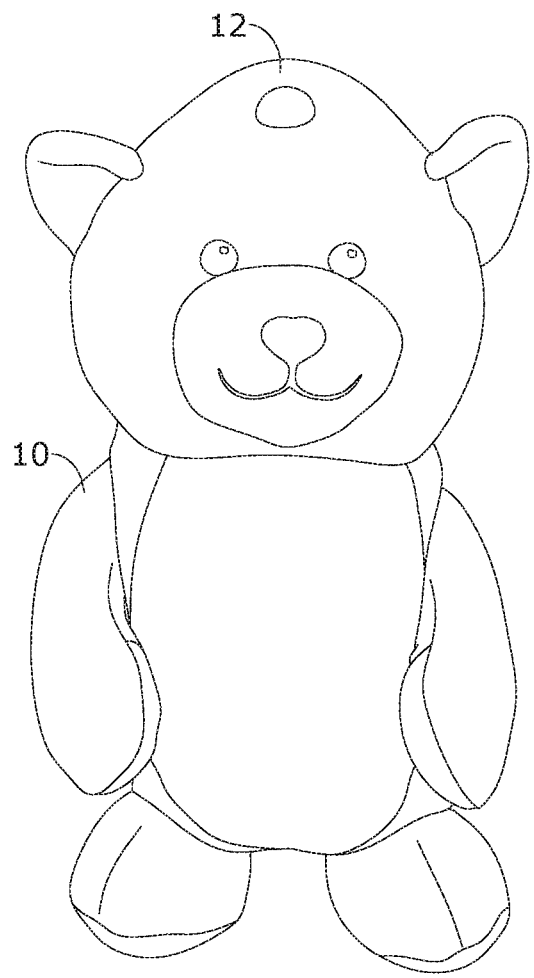
FIG. 3 is a front elevation view of an exemplary embodiment of the present invention.
Figure 4:
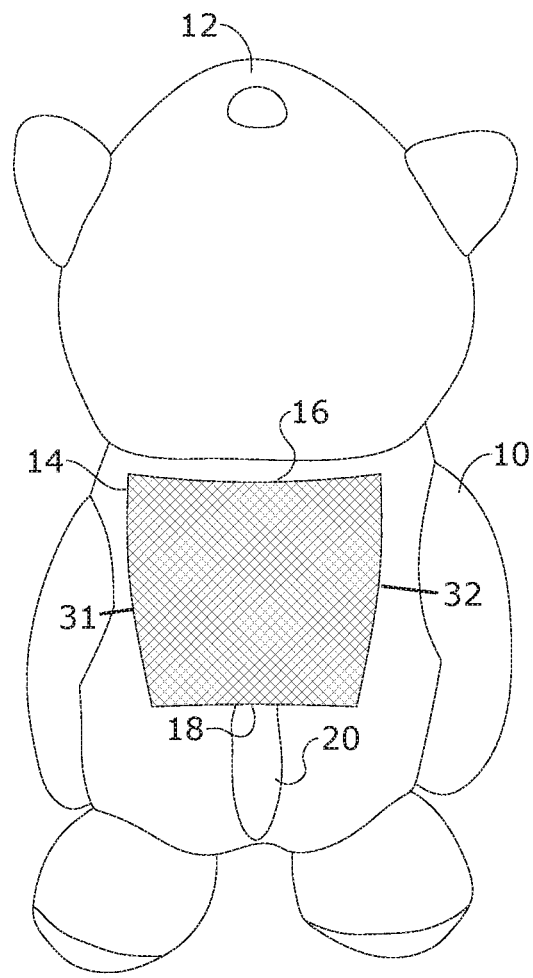
FIG. 4 is a rear elevation view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a therapeutic pouch defining a cavity for slidably receiving an intravenous therapy equipment, such as an IV bag. A front portion of the therapeutic pouch provides a comforting presentation for the patient, while the rear portion of the therapeutic pouch provides a visibility pouch for securing the IV bag and allowing a healthcare provider visibility of the administration of the fluids retained by the IV bag. The visibility pouch may provide an upper opening and an opposing lower opening, both communicating with the cavity for enabling the IV bag to protrude therefrom and access to IV tubing and ports, respectively. An upper portion of the therapeutic pouch provides a hanging loop for working in unison with the IV bag hole for enabling support from an IV stand or the like.

Referring to FIGS. 1 through 6, the present invention may include a therapeutic pouch 10 having a front portion 40, a rear portion 50, a lower portion 60, and an upper portion 70. It should be understood by those skilled in the art that the use of directional terms such as upper, upward, top, lower, bottom, downward, top, front, rear, and the like are used in relation to the illustrative embodiments as they are depicted in the figures, the upward direction (or upper) being toward the top of the corresponding figures, the downward (or lower) direction being toward the bottom of the corresponding figures, and so on.

The therapeutic pouch 10 may provide an inner cavity 20 defined by the front, rear, lower, and upper portions 40, 50, 60, and 70. The cavity 20 may be dimensioned and adapted to slidably receive an intravenous therapy (IV) bag 24.

The upper portion 70 may provide a hanging loop 12 dimensioned and adapted align with, and in certain embodiments be at least coextensive with, an IV bag hole 26 of the IV bag 24 housed in the cavity 20. The hanging loop opening 12 may also be dimensioned and adapted to removably engage a stand hook 22 or equivalent of an IV stand. The hanging loop 12 may include a grommet for reinforcing associated opening.

Figure 5:
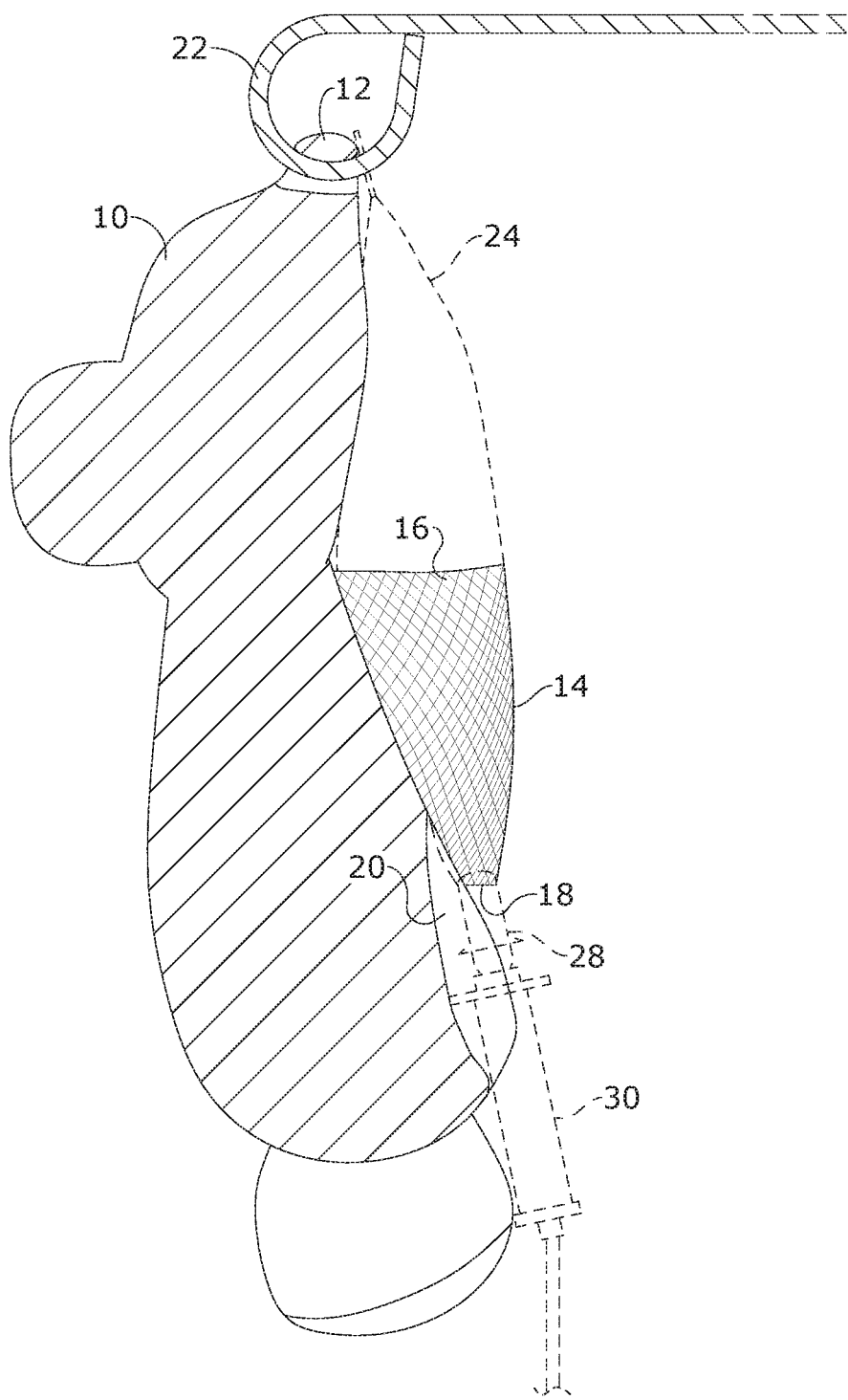
FIG. 5 is a section view of an exemplary embodiment of the present invention, taken along line 5-5 in FIG. 1, with bag 24 reduced to dashed lines for clarity.
Figure 6:
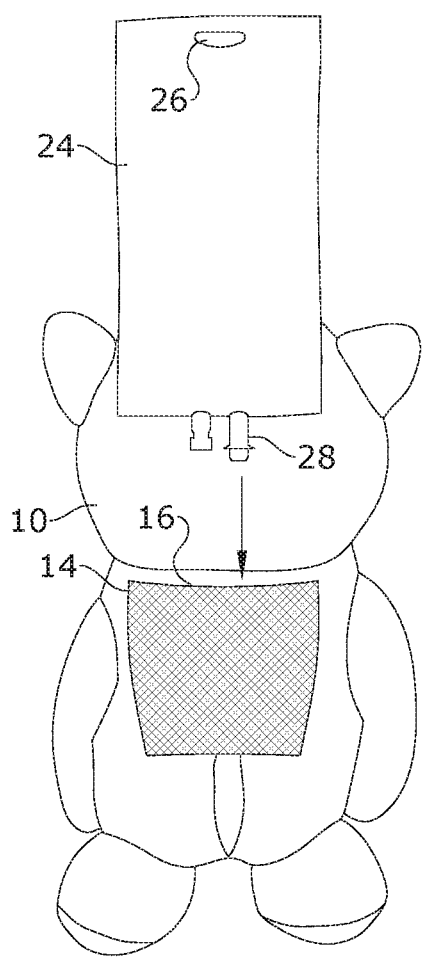
FIG. 6 is a rear view of an exemplary embodiment of the present invention, showing the insertion of bag 24 into pouch 14 prior to spiking.
Figure 7:
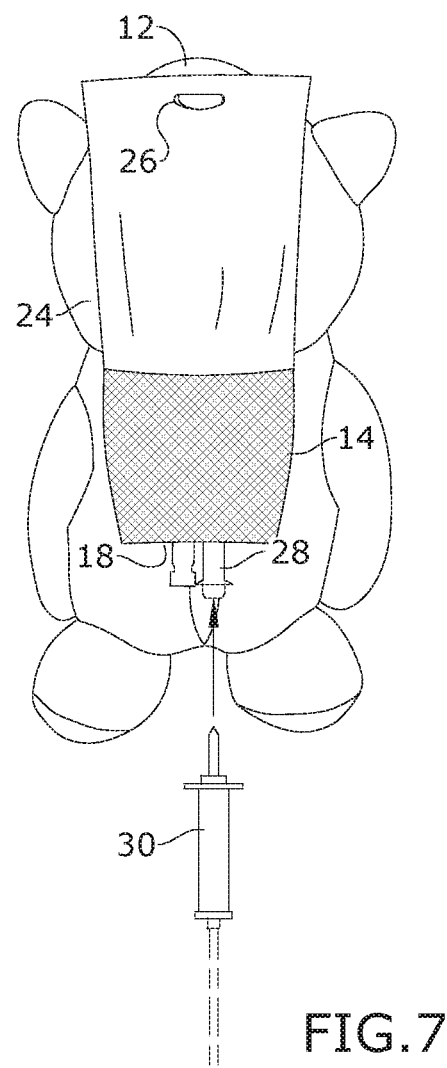
FIG. 7 is a rear view of an exemplary embodiment of the present invention, showing port 28 being spiked once in place.

The rear portion 50 may be substantially a void communicating to the cavity 20 so as to provide space for a portion of the IV bag 24 housed in the cavity 20 to protrude from the void, as illustrated in the FIGS. Spanning a portion of the void may be a visibility material (such as a mesh or other material providing users visibility therethrough, such as a transparent plastic or the like) extending from a first edge 31 of the front portion to an opposing second edge 32 of the front portion, forming a visibility pouch 14 to restrain and secure the IV bag 24 housed in the cavity, as illustrated in FIG. 5. The resulting visibility pouch 14 provides an upper opening 16 from which the IV bag 24 may protrude. The visibility pouch 14 may provide a bottom opening 18 communicating with the cavity 20, and so an IV bag port 28 may be slidably received for interconnecting with the IV bag 24 and an IV bag spike 30.

The front portion 40 may include elastic material taking the shape of a stuffed animal body including, in certain embodiments, a stuffed head, arms and legs or the like. The stuffed animal style front portion 40 may be made in the usual way using a sewing machine and stuffing. The visibility material/fabric or sleeve is attached to the rear portion 50 of the therapeutic pouch 10, forming a loose pouch or sleeve with openings at the top and the bottom of the visibility material/fabric to insert the IV bag or medication. The IV tubing and port 28 will exit the bottom portion 60 of the therapeutic pouch 10. The hanging loop 12 may be provided in the head of the stuffed animal shape. Overall, the front portion 40 is dimensioned and adapted to take the shape of different types of stuffed animals that are visually appealing to the patient so as to foster a feeling of comfort and familiarity for the patient. Thus, the stuffed animals could be created in different designs more friendly to, say, geriatric adults or teen populations (e.g., flowers, sports items, hobby items, etc.). Likewise, the present invention could be made much larger so it would fit over IV pumps, feeding pumps, oxygen tanks and other medical equipment.

A method of using the present invention may include the following. The therapeutic pouch 10 disclosed above may be provided. A user may slide the IV bag 24 into the visibility pouch 14 on the rear portion 50, so that the IV bag 24 is housed in the cavity 20 with the opening of the port 28 of the IV bag 14 adjacent the bottom opening 18 along the lower portion 60 of the therapeutic pouch 10. The IV bag 24 may then be "spiked" in the usual way and tubing primed as usual by the health care provider. The health care provider may monitor medication/fluid administration through the void and/or visibility pouch 14 along the rear portion 50. The present invention hangs together with the IV bag 24 by way of the hanging loop 12 on the IV pole/stand 22 and does not take the weight of the IV bag 24.

It should be understood, of course, that the foregoing relates to exemplary embodiments of the invention and that modifications may be made without departing from the spirit and scope of the invention as set forth in the following claims.

What is claimed is:

1. A system for comforting a patient of intravenous therapy, comprising:
   a therapeutic pouch defining an inner cavity, wherein the inner cavity is adjacent a front surface of the therapeutic pouch, wherein the front surface provides a stuffed animal body shape, and wherein a rear portion of the therapeutic pouch provides a void communicating with the inner cavity;
   a visibility material extending between opposing peripheries of the void, wherein the visibility material defines a sleeve having an upper opening and an opposing lower opening, wherein when an intravenous bag is engaged by the visibility material a lower portion of the intravenous bag is urged to protrude into the inner cavity, while about half of the intravenous bag protrudes beyond the upper opening; and
   a hanging loop in the therapeutic pouch, wherein the hanging loop aligns with a hanging hole of the intravenous bag.

2. A method of comforting a patient of intravenous therapy, comprising:
   providing the system of claim 1;
   sliding the intravenous bag into the inner cavity so that the hanging loop aligns with the hanging hole of the intravenous bag; and
   sliding the hanging loop and the hanging hole on a hook of a stand associated with the intravenous therapy so that the stuffed animal body shape is facing the patient.

3. The method of claim 2, wherein the visibility material is mesh.

4. The method of claim 3, further comprising sliding a bag port of the intravenous bag through the lower opening.

5. The system of claim 1, wherein the lower opening is approximately at a midsection level of the stuffed animal body shape so that said lower portion is urged into a lower portion of the inner cavity.

6. The system of claim 1, wherein the visibility material is mesh.

7. The system of claim 6, the upper opening is adjacent to a shoulder level of the stuffed animal body shape.

* * * * *